United States Patent
Salvatori et al.

(10) Patent No.: US 6,422,669 B1
(45) Date of Patent: *Jul. 23, 2002

(54) CARRYING CASE FOR DEFIBRILLATOR

(75) Inventors: Phillip H. Salvatori, SW. Salem; Martin John Maiers, Newberg; Stephen V. Cooper, Amity; Jonathan Neal Andrews, McMinnville, all of OR (US)

(73) Assignee: Koninklijke Philips Electronics N.V., Eindhoven (NL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/188,471

(22) Filed: Nov. 9, 1998

(51) Int. Cl.[7] .................................................. A47B 75/00
(52) U.S. Cl. ....................................... 312/213; 206/320
(58) Field of Search ................................ 312/209, 107, 312/108, 111, 223.6, 223.1, 213; 206/570, 305, 320, 349, 351; 220/554, 503, 505, 4.02

(56) References Cited

U.S. PATENT DOCUMENTS

| | | | | |
|---|---|---|---|---|
| 3,606,506 A | * | 9/1971 | Ungaro | 312/111 |
| 4,194,628 A | * | 3/1980 | Campos | 206/570 |
| 4,658,956 A | * | 4/1987 | Takeda et al. | 206/320 |
| 4,855,845 A | * | 8/1989 | Thrush | 206/320 X |
| D305,796 S | | 1/1990 | Forland et al. | D24/17 |
| D337,822 S | | 7/1993 | Janke | D24/185 |
| 5,314,070 A | * | 5/1994 | Ciarlei | 206/570 |
| D348,104 S | | 6/1994 | Olsen | D24/167 |
| 5,458,408 A | | 10/1995 | Cooper et al. | 312/213 |
| 5,464,428 A | | 11/1995 | Hill | 607/1 |
| 5,574,252 A | | 11/1996 | Hill | 174/51 |
| D377,097 S | * | 12/1996 | Olson et al. | D24/167 |
| 5,603,402 A | * | 2/1997 | Cuneo | 206/320 |
| 5,667,121 A | | 9/1997 | Hill | 225/43 |
| D392,739 S | | 3/1998 | Bertagnole et al. | D24/167 |
| 5,801,331 A | * | 9/1998 | Zachrai | 312/223.1 X |
| 5,808,865 A | * | 9/1998 | Alves | 206/320 X |
| 5,857,568 A | * | 1/1999 | Speirs | 206/320 |
| 5,884,772 A | * | 3/1999 | Floyd et al. | 220/4.02 X |
| 5,960,952 A | * | 10/1999 | Chen | 206/320 |

* cited by examiner

*Primary Examiner*—Peter M. Cuomo
*Assistant Examiner*—Stephen Vu

(57) ABSTRACT

A carrying case for external defibrillator having at least one surface-mounted operational features. The carrying case includes a main interior compartment that securely holds a defibrillator such that at least one of surface-mounted operational features of the defibrillator is accessible to the operator without removing the defibrillator from the carrying case. This enables the defibrillator to be used while held in said main interior compartment. At least one storage compartment is provided having an interior dimension adapted to hold at least one item associated with the defibrillator. The storage compartment has an associated aperture formed on an exterior of the carrying case such that the storage compartment is accessible from an exterior of the carrying case.

12 Claims, 5 Drawing Sheets

FIG. 6
FIG. 7
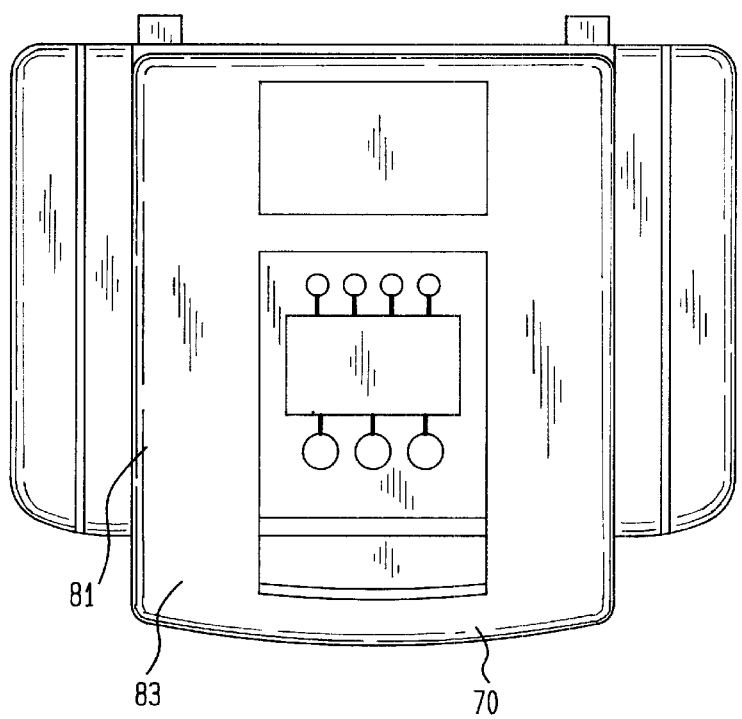
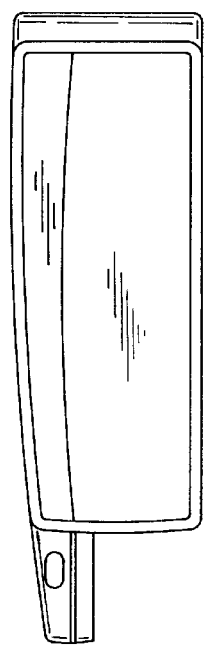
FIG. 8
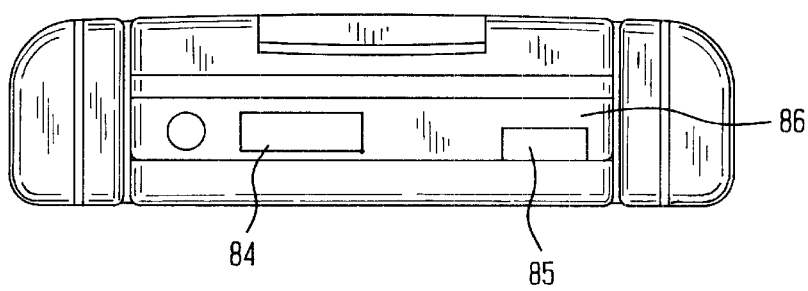

CARRYING CASE FOR DEFIBRILLATOR

BACKGROUND OF THE INVENTION

1. Field of the Invention

The present invention relates generally to a carrying case for portable electronic equipment and, more particularly, to a carrying case for a portable external defibrillator.

2. Related Art

Sudden cardiac arrest is a disruption of the heart's functioning that causes a lack of blood flow to vital organs. In a majority of instances, sudden cardiac arrest is manifested as an abnormal or chaotic heart rhythm, called arrhythmia. These instances are generally identifiable by the victim's immediate loss of pulse, loss of consciousness and a cessation of breathing.

Sudden cardiac arrest has been attributed to over 350,000 deaths each year in the United States, making it one of the country's leading medical emergencies. World-wide, sudden cardiac arrest has been attributed to a much larger number of deaths each year. Unless medical intervention is initiated, sudden cardiac arrest can lead to death within a matter of minutes. To date, the average survival rate for sudden cardiac arrest remains at around 5 percent. In cities with traffic congestion and slow elevators, the survival rate is estimated to be as low as a mere 1 percent.

There are four critical components of medical treatment that must be administered to a victim of sudden cardiac arrest: (1) early access to emergency care; (2) early cardiopulmonary resuscitation to keep the blood oxygenated and flowing to the victim's brain and other vital organs; (3) early defibrillation (the application of an electrical shock to the heart) to restore the heart's regular rhythm; and (4) early access to advanced medical care. When a person is experiencing sudden cardiac arrest, the electrical activity within the heart becomes chaotic. An electric shock from a defibrillator can reorganize the electrical impulses to allow coordinated pumping action to resume. To administer this shock, special pads from a machine called a defibrillator are placed on the victim's chest, and an electric shock is sent through the victim's body from one pad to another. As used herein, the term "pads" will include both pads and paddles.

If prompt cardiopulmonary resuscitation is followed by defibrillation within about four minutes, the victim's chances of surviving sudden cardiac arrest can approach or exceed forty percent. Prompt administration of defibrillation within the first critical minutes is considered one of the most important components of emergency medical treatment for preventing death from sudden cardiac arrest.

Since prompt defibrillation is critical to survival, portable defibrillators have been developed that can be carried to the victim's location to defibrillate the victim prior to reaching a hospital. These portable defibrillators, like other sensitive electronic equipment, can fail if dropped or bumped during transportation or exposed to adverse environmental conditions. Additionally, various wires, pads and other supplies are needed to operate the portable defibrillator and must be transported along with the defibrillator.

Carrying cases have been developed to protect portable defibrillators and associated supplies during transportation and while in storage. One of the more common carrying cases is made of fabric, commonly referred to as a soft side case, in which the defibrillator is placed. Soft side cases typically are formed from a fabric envelope without significant structure and are occasionally provided with a large pocket, in which associated supplies, such as cables and pads, are stored. Soft sided cases, while occasionally adequate to protect the defibrillator against the elements, offer very little protection to the defibrillator in the event the defibrillator is dropped or bumped during transportation. Additionally, supplies and cables within the supply pockets often become tangled, hindering deployment of the defibrillator.

Another common case for transporting and storing portable defibrillators is a hard sided case having two symmetrical or similar halves hinged together, similar to a suitcase. Although this case effectively protects the defibrillator against damage during transportation, it has proved to be unsatisfactory in use. Specifically, to deploy the defibrillator, it is necessary to unlatch and open the case (i.e. separate the two halves of the case to expose the enclosed defibrillator), remove the defibrillator, close the case and set the case aside. This process consumes valuable time which could be spent defibrillating the victim or otherwise attempting to save the victim's life. Additionally, the case must be managed at the scene; in a crowded and hectic environment, the case can occupy valuable space that could be used by medical personnel or other instrumentation.

Accordingly, it would be advantageous to have a carrying case for a portable external defibrillator that is compact, easy to use, and that will adequately protect the defibrillator against hazards associated with transportation and storage. It would also be advantageous to have a carrying case that will not contribute significantly to cluttering the scene of the medical emergency nor extend the amount of time required to set up the defibrillator prior to operation. Additionally, it would be advantageous to have a carrying case that would provide for organization of the wires, pads and other supplies typically used in connection with operation of the defibrillator.

SUMMARY OF THE INVENTION

The present invention is a carrying case for an external defibrillator or other electronic device that is compact, easy to use, and that will adequately protect the device during transportation and use. The carrying case includes a body structure that defines a main compartment dimmensioned to retain the defibrillator such that at least one surface-mounted operational feature of the defibrillator is immediately exposed and accessible without removing the defibrillator from the carrying case. Also included are storage compartments, each dimmensioned to receive, store and retain items operationally associated with the defibrillator. Each storage compartment has an aperture formed on an exterior of the carrying case such that each storage compartment is immediately and separately accessible from an exterior of the carrying case.

Generally, the surface-mounted operational features include an operational control panel of the defibrillator. Here, a side of said main compartment adjacent to the operational control panel is configured with an aperture sufficiently large to provide access to the panel. In some embodiments, a zippered flap covers the aperture. The surface-mounted operational features may also include, for example, a battery pocket access door. In this embodiment, a side of the main compartment adjacent to the battery pocket is configured to include an aperture sufficiently large to enable the operator to quickly and easily replace a battery in the battery pocket. Other operational features may include, for example, display panels, speakers, electrical and data communication ports, etc.

The carrying case includes one or more doors each associated with a storage compartment. The doors are movably mounted on the body to be located in a plurality of positions. When in a closed position, the door obscures the aperture of the associated storage compartment preventing access to items stored therein; when in an open position the door is adjacent to the aperture, allowing such access to the stored items. The items may be any item operationally related to the defibrillator. Preferably, such items stored in each storage compartment will include a combination of one or more supplies, cables and pads that are functionally related. For example, in one storage compartment monitoring equipment is stored. Such monitoring equipment may include, for example, an EKG cable and a finger $SpO_2$ cuff cable. It is also preferable that one of the storage compartments is dimensioned to store replaceable items. In certain embodiments, a zipper is provided in place of such doors.

In an alternative embodiment, at least one storage compartment is constructed and arranged to store one or more connectable items adapted to be operationally connected to the defibrillator. This storage compartment is formed at a location in the carrying case body structure to enable the connectable items to be and remain connected to the defibrillator while stored in the storage compartment.

Preferably, a portion of the body structure is comprised of a material enabling an image of items stored in certain "transparent" storage compartments to be externally visible. This enables an operator to view contents of such transparent storage compartments without opening the associated door.

In another aspect of the invention a carrying case for a defibrillator is disclosed. The carrying case includes a body structure constructed and arranged to include a first compartment configured to detachably secure the defibrillator within the compartment. The first compartment is defined by walls of the body structure, certain of walls of which have apertures to provide direct and immediate operator access to one or more control panels of the defibrillator. A plurality of storage compartments are also defined in the carry case body structure. Each of these storage compartments is configured to store one or more supplies, cables and pads. Importantly, each storage compartment has at least one wall defining an exterior of the carrying case, the exterior wall having an aperture adapted to be covered by a door movably mounted on the body structure. This enables each of the storage compartments to be separately accessible from the exterior of the carrying case without having to reposition the defibrillator or access any other storage compartment in the carrying case. Preferably, either or both the body structures and doors comprises a transparent portion enabling an operator to view the content of certain storage compartments without opening the door associated with that storage compartment.

In another aspect of the invention a combination of elements including a portable defibrillator and a carrying case is disclosed. The carrying case includes a semi-rigid sub-frame structure defining a plurality of individual and separately accessible compartments, at least one of which is adapted to accommodate the defibrillator in such a manner as to enable access to one or more surface-mounted operational features, including a control panel of the defibrillator without removal of the defibrillator from the carrying case. Embodiments of the carrying case also include a flexible outer cover covering at least a portion of the sub-frame forming exterior walls and/or doors of certain storage compartments. In one embodiment, at least a portion of the flexible outer cover disposed over some of the storage compartments is transparent to facilitate viewing of contents of such compartments. In one particular embodiment, the sub-frame structure further defines a storage compartment constructed and arranged to accommodate replaceable items associated with the operation of the defibrillator.

Further features and advantages of the present invention as well as the structure and operation of various embodiments of the present invention are described in detail below with reference to the accompanying drawings. In the drawings, like reference numerals indicate identical or functionally similar elements. Additionally, the left-most one or two digits of a reference numeral identifies the drawing in which the reference numeral first appears.

BRIEF DESCRIPTION OF THE DRAWINGS

This invention is pointed out with particularity in the appended claims. The above and further advantages of this invention may be better understood by referring to the following description when taken in conjunction with the accompanying drawings, in which:

FIG. 6 is a top view of the carrying case of FIG. 5;

FIG. 7 is a side view of the carrying case of FIG. 5;

FIG. 8 is a front end view of the carrying case of FIG. 5; and

DETAILED DESCRIPTION

Figure 1:
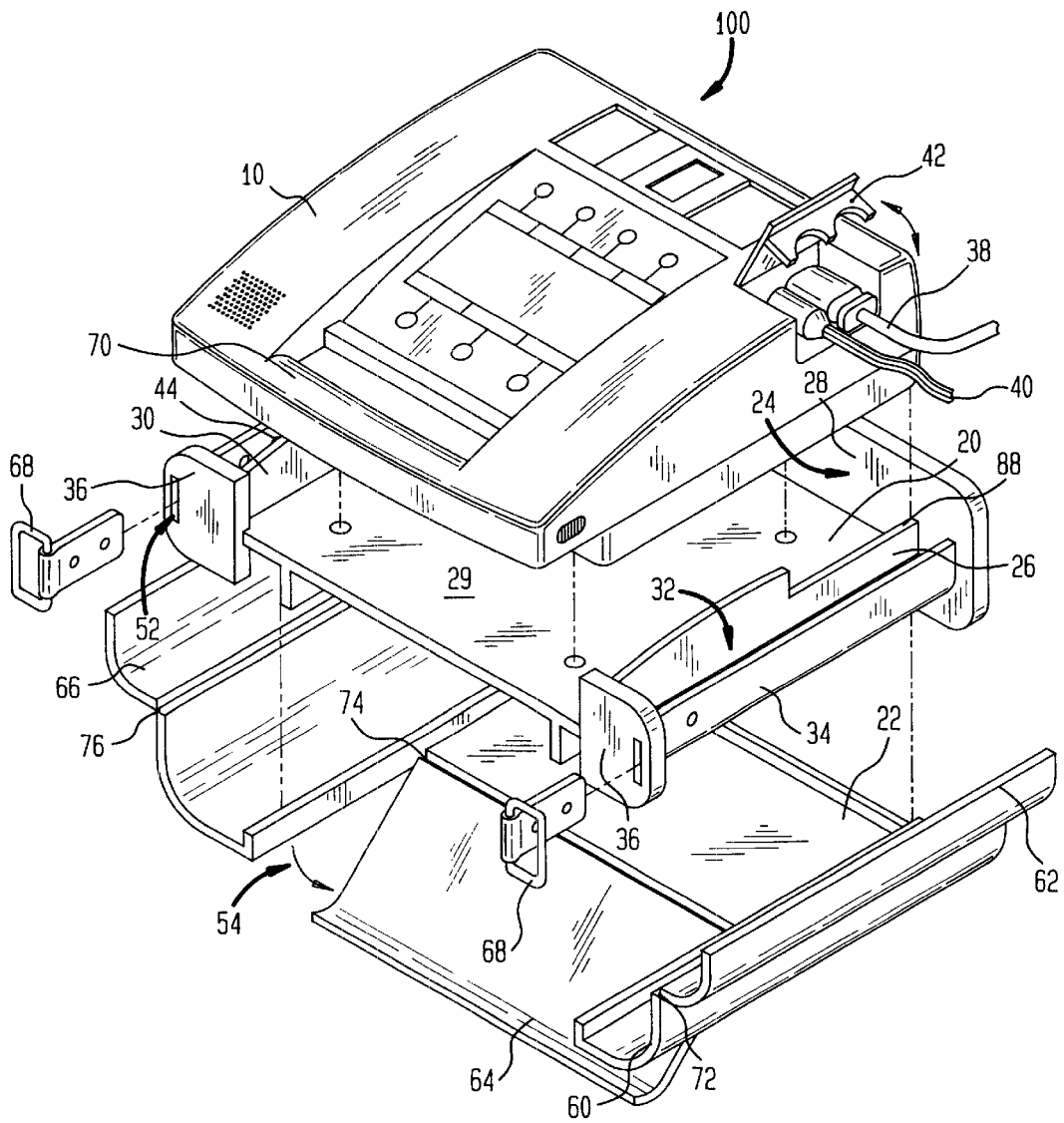
FIG. 1 is an exploded, perspective view, of the carrying case according to one embodiment of the invention for use with a portable external defibrillator.

The present invention is a carrying case for an external defibrillator or other electronic device that is compact, easy to use, and that will adequately protect the device during transportation and use. FIG. 1 is an exploded perspective view of one embodiment of the carrying case of the present invention for use with a portable external defibrillator. As shown in FIG. 1, a carrying case 100 includes a rigid sub-frame structure 20 and a flexible outer cover 22 formed over the sub-frame structure 20. The sub-frame structure 20 has a pair of side walls 26, 30 that cooperate with a back wall 28 and central floor 29 to define a central compartment 24 for receiving a portable defibrillator 10. Cushioning materials such as bumpers (not shown) may be included to protect the defibrillator from its anticipated environment. Optionally, a layer of cushioning foam may be used to line the interior of the central compartment to partially isolate the defibrillator and to protect the defibrillator from ordinary bumps and drops. Other materials that absorb or deflect forces experienced by the carry case 100 during its anticipated transportation, use and storage may also be used, as is known in the art.

The portable defibrillator 10 is removably secured in the central compartment 24 with screws, bolts, rivets, tie downs or other suitable fasteners. Preferably, captive hardware is used. Optionally, hooks or other cooperative retaining mechanisms could be formed on the portable defibrillator 10 and in the central compartment 24 to retain the portable defibrillator 10 within the central compartment 24. Likewise, straps, elastic bands, magnets, or virtually any other device capable of securely retaining the portable defibrillator 10 within the central compartment 24 could be used in connection with or instead of the fasteners.

Significantly, carrying case 100 is configured such that the operational control panels of the portable defibrillator 10 are accessible without removing the portable defibrillator 10 from the carrying case 100. In the embodiment illustrated in FIG. 1, the central compartment 24 does not include a top side, cover or panel. As a result, when defibrillator 10 is secured within the compartment 24, the top surface 81 of the defibrillator is permanently exposed, providing the operator with complete and immediate access to the operational panel 82 on the top surface 81.

Figure 4:
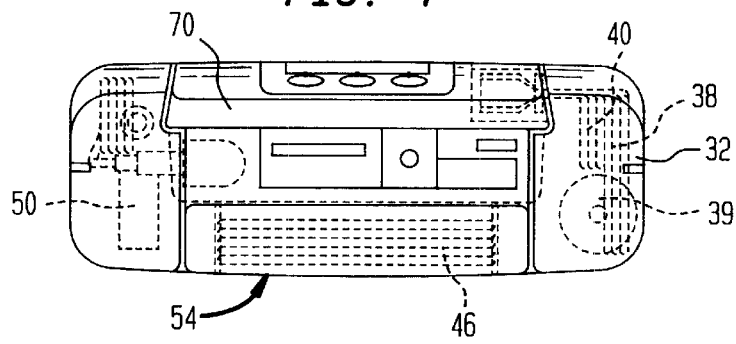
FIG. 4 is a front end view of the carrying case of FIG. 1 containing the portable external defibrillator and associated wires, pads and supplies.

It is preferable that all sides of the carrying case compartment 24 that are adjacent to operational features of the defibrillator 10 have openings sufficient to expose such features. For example, on the left side of top surface 81 is a speaker 83 which is also exposed when the defibrillator 10 is secured within compartment 24. Also, as shown in FIGS. 1 and 4 the front side of compartment 24 is also substantially open to provide access to a PCMCIA card 84 and battery 85 located below handle 70 on the lower front surface of the defibrillator 10. Thus, the carrying case 100 facilitates rapid deployment of the portable defibrillator while providing optimal protection for the defibrillator during transportation.

In accordance with the present invention, the carrying case 100 includes a number of individual storage compartments for supplies, cables, pads and the like, each of which is separately accessible from the exterior of the carrying case without having to reposition or otherwise move the defibrillator 10. Each storage compartment is preferably dimensioned to store one or more specific items. It is also preferable that the items to be stored in each compartment are functionally related. For example, monitoring equipment such as EKG cable 38 and finger cuff cable 40 may be stored in the same compartment. Similarly, all replaceable items may be stored in one compartment. Other arrangements are considered to be within the scope of the present invention. It is also preferable that compartments storing items which are to be connected to the defibrillator are configured to allow such connection while the items are stored in the compartment. As will be described below, such compartments would be located adjacent to the appropriate defibrillator ports and include interior walls having apertures, through-holes or the like to facilitate such connections. To provide independent accessibility, each individual storage compartment is provided with a door, cover, or zippered access. Thus, in a preferred embodiment, the present invention provides individual, externally-accessible storage compartments each dimensioned to hold functionally related items adjacent to appropriate surfaces of the defibrillator 10 to maintain connections with the defibrillator 10 while stored.

A right compartment 32 is formed adjacent the central compartment 24 to the right of the central compartment when viewed from the front. The right compartment 32 is defined by the wall 26, the back wall 28, a right external wall 34 and a front wall 36. Optionally, the wall 26 could be wholly or partially eliminated and the left portion of the right compartment could be at least partially defined by the right edge of the defibrillator contained in the central compartment 24. The front wall 36 in the illustrated embodiment extends from the front surface 86 of the defibrillator and does not substantially cover the front surface of the defibrillator to provide the noted access to ports on the front surface 86 of the defibrillator 10. The front wall could optionally extend wholly across the front of the defibrillator if access to the front of the defibrillator during normal operation was not required.

Figure 2:
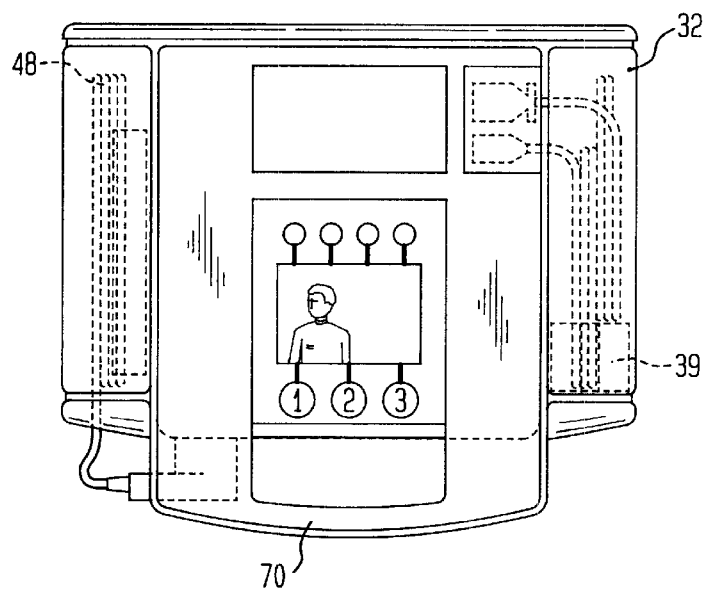
FIG. 2 is a top view of the carrying case of FIG. 1 containing the portable external defibrillator and associated wires, pads and supplies.
Figure 3:
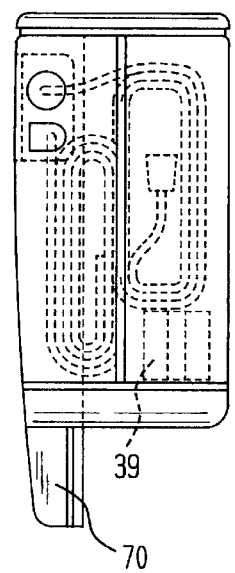
FIG. 3 is a side view of the carrying case of FIG. 1 containing the portable external defibrillator and associated wires, pads and supplies.

The right compartment 32 is configured to store or dimensioned to store/hold an EKG cable 38 and a finger cuff cable 40 during transportation and storage. In one embodiment, the portable defibrillator 10 is provided with a locking door 42 to secure the EKG cable 38 and finger cuff cable 40 in engagement with mating receptacles on the portable defibrillator 10. The finger cuff cable 40 may be eliminated if the defibrillator is not equipped to obtain $SpO_2$ data. A spare roll of paper 39 (illustrated in FIGS. 2–4) for the defibrillator printer may be contained in the right compartment 32 as well. If the carrying case 100 is designed for use with an electronic device other than a portable defibrillator 10, the right compartment could be configured, constructed and arranged to contain other appropriate cables, supplies, or items used in connection or combination with the electronic device.

The right compartment 32 illustrated in FIG. 1 does not have a floor formed from the sub-frame structure 20. Instead, the bottom of the right compartment 32 is formed by the flexible outer cover 22. A floor could be provided, however, if desired, without unduly complicating the manufacturing process. Omitting the floor from the sub-frame structure 20 reduces the overall weight while only somewhat reducing the strength of the resulting carrying case 100. To further reduce the weight of the carrying case 100, portions of the walls could be removed, such as by forming apertures in the walls. As shown in FIG. 1, an aperture in the form of a cut-out 88 is provided in wall 26 to enable cables 38 and 40 to be connected to the defibrillator 10 while stored in right compartment 32. Such an arrangement eliminates the need to make such connections at the time the defibrillator is operated.

A left compartment 44 is formed to the left of the central compartment 24 when viewed from the front. In the illustrated embodiment, the left compartment 44 is formed to be the mirror image of the right compartment 32 but is designed to contain defibrillator cables and a spare battery 50. In alternative embodiments, spare battery 50 is stored in a lower compartment 54 described below. If the carrying case 100 were designed to be used with an electronic device other than a portable defibrillator 10, the left compartment could be configured, constructed and arranged to house or transport other supplies, cables, or items. The section of the front wall 36 forming the left compartment 44 preferably has a slot 52 through which the defibrillator cable can pass to prevent the cable 48 from becoming detached from the portable defibrillator 10 during use.

A lower compartment 54 is formed below the central compartment 24. The lower compartment may optionally be extended to also be formed below portions of one or both of the right compartment 32 and the left compartment 44 by providing the respective compartment with a floor formed from section of the sub-frame. The lower compartment is designed to hold replacement defibrillator pads 46 and other replaceable supplies that may be required by the operator of the defibrillator, such as gloves, etc. Optionally, the lower compartment 54 may be sized to contain pads without requiring the pads to be folded prior to insertion. The lower compartment is defined on top by the sub-frame underlying the central compartment; in the back, by the back wall 28; and on the sides, by extensions of walls 26 and 30.

In a preferred embodiment, the footprint of the carrying case 100 is not significantly larger than the portable defibrillator so that the carrying case 100 does not unduly contribute to cluttering the otherwise hectic and crowded scene associated with reviving the victim. Thus, in the illustrative embodiment lower compartment 54 is provided rather than providing a large side compartment.

The walls of the sub-frame 20 defining the various compartments may be formed independently and attached using appropriate fastening members such as rivets, screws, bolts, etc. or may be adhered or joined using ultrasonic welding, an appropriate adhesive such as cyanoacrylate, or by any other known method.

A semi-rigid molded material 60 is preferably wrapped around the outside of the sub-frame structure 20 to define the shape and appearance of the carrying case 100. Although a flexible molded material is preferred, any material, rigid or flexible, that is capable of retaining the components within the respective compartments may be used. Examples of suitable material include plastics, high durometer rubber, canvas, etc. In one preferred embodiment, thermally-formed, fabric covered foam is utilized. Preferably, at least portions of the flexible molded material are formed of a clear material such as a clear plastic or plexiglass so that the operator can view the content of the compartment without opening the compartment. By using a transparent material, the status of the supplies within the compartment is immediately apparent to the user of the defibrillator. This is especially helpful for the situation where the supplies, such as replacement batteries, are dated and must be replaced after expiration of a particular period of time. The transparent portion of the flexible molded material may be bonded or attached to the remainder of the material by sewing, adhesives, thermal bonding, or any known appropriate method, depending on the type of materials involved.

In accordance with the illustrative embodiment, each compartment has a door moveably mounted to the carrying case 100 to provide access separately to the contents of each compartment. In the illustrative embodiment, access flaps 62, 64, 66 are formed for the left compartment, lower compartment and right compartment, respectively, and are rotatably connected to the flexible molded material. Access flaps are delineated from the remainder of the flexible molded material 60 by hinge lines 72, 74 and 76, respectively. Hinge lines 72, 74, 76 creased, scored or living hinges formed better integral section of material. These types of hinges are preferable in certain applications because of their ability to prevent penetration into the compartment of dust and moisture from the surrounding environment. Hinge lines 72, 74, 76 may also be formed by any other type of know hinge, such as metallic hinges or other structures capable of rotatably coupling the access flaps 62, 64, 66 to the rest of the flexible molded material. If desired, a flap may be provided over the central compartment 24 to enclose the portable defibrillator 10 as well.

Optionally, the flaps may be formed such that closure of the access flaps causes the respective compartment to be sealed from the environment. Forming seals on access flaps may be done in any known manner. Likewise, if desired, one or more of the access flaps 62, 64, 66 could be provided with a locking mechanism to prevent unauthorized access to the respective compartment.

The sub-frame structure 20, flexible molded material 60 and access flaps 62, 64, 66 together provide a plurality of individual compartments each externally accessible and configured to hold functionally related items together. Importantly, the access flaps provide access to the individual compartments to an operator so that the operator need not sort through extraneous items to locate the appropriate accessory. This provides for better supply management, improved cable strategy and easier operation, all of which contribute to reducing the amount of time required to set up and begin use of the defibrillator when responding to a medical emergency. Also, having independently accessible compartments reduces the risk of spillage and hence contamination of the contents of the compartments by the surrounding environment.

A strap 68 may be attached to the front wall portions 36 to facilitate transportation of the portable defibrillator 10 and carrying case 100. During transportation of the defibrillator, the user will typically carry the defibrillator 10 and carrying case 100 by the strap over the person's shoulder or by a handle 70 on the defibrillator 10. In this situation, either the left compartment 44 or the right compartment 32 will form the leading surface of the carrying case 100 during transportation, and thus the surface that is the most likely to impact on a stationary object, such as a desk, table, etc. Accordingly, the compartments themselves serve the dual purpose of forming bumpers to protect the defibrillator from impact during transportation.

Although the carrying case disclosed in this application has been explained with respect to a portable external defibrillator, the principles described herein could easily be applied to cases for non-portable defibrillators, or to carrying cases for other medical instruments and electronic devices such as EKG monitors, lap-top computers, palm-top computers, printers, portable stereophonic equipment, portable video equipment, and other types of consumer or professional electronic equipment.

Likewise, although the carrying case described in detail herein has a central compartment designed to accommodate the electronic device, the carrying case could be modified to accommodate more than one electronic device, such as a defibrillator and a cellular phone, or could be modified to accommodate the electronic device in a compartment other than the central compartment. For example, the lower compartment or one of the right and left compartments could be formed to accept and retain the electronic device.

Finally, the carrying case is not necessarily limited to having four compartments, as described herein. Any number of compartments could be formed, for example, by bifurcating or otherwise separating one or more of the compartments. Likewise, it may be possible to form fewer compartments by eliminating portions of the walls separating the various compartments. Accordingly, the number of compartments could be modified to suit the particular application and the particular electronic device for which the carrying case is designed.

Figure 5:
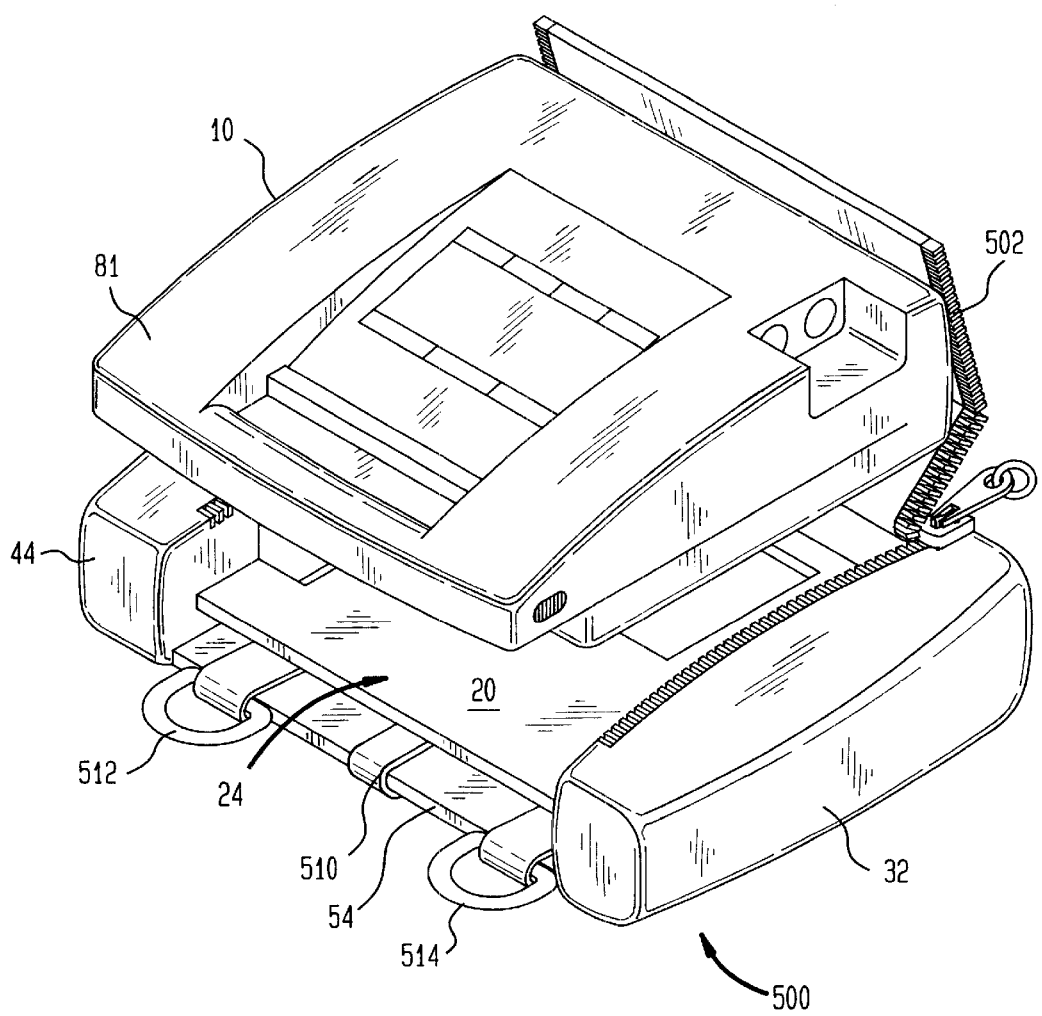
FIG. 5 is a perspective view, of an alternative embodiment of the carrying case of the invention for use with a portable external defibrillator.
Figure 9:
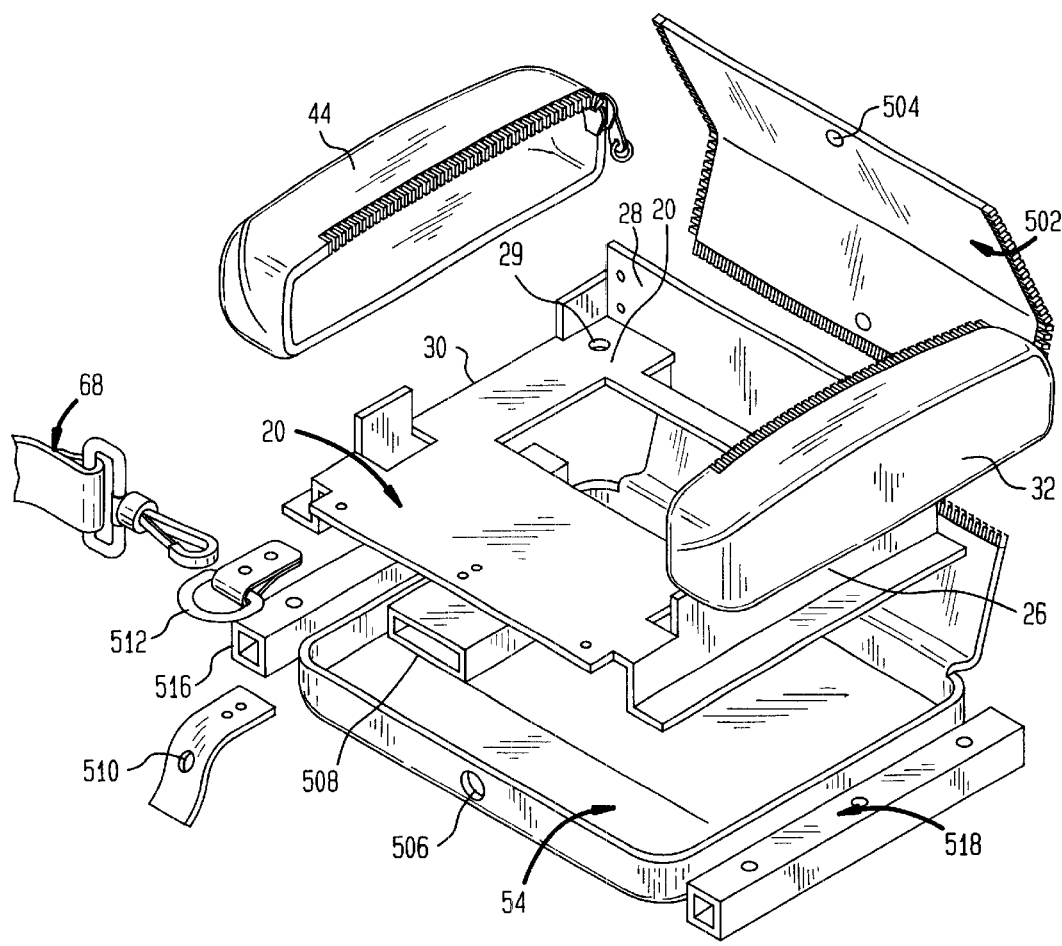
FIG. 9 is an exploded, perspective view, of the carrying case illustrated in FIG. 5.

An alternative embodiment of the carrying case of the present invention will be briefly described with reference to FIGS. 5–9. FIG. 5 is a perspective view of an alternative embodiment of carrying case 500 for use with a portable external defibrillator. FIGS. 6–9 are a top, side, front and an exploded perspective view, respectively, of the carrying case 500.

Carrying case 500 includes a rigid sub-frame structure 20 and a number of self-contained compartments secured thereto. As noted above, the present invention provides individual, externally-accessible storage compartments each dimensioned to hold items related to the defibrillator 10. To provide independent accessibility, each individual storage compartment is provided with a centrally-located zipper rather than a compartment door or flap as in the above described embodiment. In contrast to the above embodiment, each compartment in carrying case 500 is individually complete; that is, the carrying case is modular, reducing the time and cost associated with assembly. The compartments are preferably made of thermally-formed, fabric covered molded foam and are primarily zippered compartments.

The sub-frame structure 20 has a pair of side walls 26, 30 that cooperate with a back wall 28, central floor 29 and side compartments 44 and 32 to define a central compartment 24 for receiving portable defibrillator 10. The portable defibrillator 10 is removably secured in the central compartment 24, preferably with captive hardware, although any type of fasteners such as those noted above may be used to retain the portable defibrillator 10 within the central compartment 24.

As with the above embodiment, carrying case 500 is configured such that the operational control panels of the portable defibrillator 10 are accessible without removing the portable defibrillator 10 from the carrying case 500. However, in the embodiment illustrated in FIGS. 5–9, central compartment 24 includes a top cover 502 zippered to side compartments 44, 32 to protect the top surface 81 of the defibrillator 10. As shown in FIG. 5, looped pull-tabs are preferably provided to facilitate locating and grasping the zipper and operating the top cover 502. Preferably, the top cover 502 is removably secured to the other components of carry case 500, such as with a snap connector 504 that mates with a corresponding snap connector 506 on lower compartment 54. This enables top cover 502 to be easily and quickly removed from the carry case 500, exposing the top surface 81 of defibrillator 10.

As shown, top cover 502 includes two flaps, one to cover a rear portion while the other covers the top of defibrillator 10. In one preferred embodiment, the top flap of the top cover 502 includes a see-through pouch for storing a quick reference instruction card while the rear flap includes a pouch that retains a set of pre-connected pads. This facilitates the quick application of a shock to a waiting victim by eliminating the time associated with removing the pads from a storage compartment and attaching them to the defibrillator 10.

A lower compartment 54 is formed below the central compartment 24. The lower compartment 24 includes a battery pouch 508 for receiving a spare battery (not shown). The lower compartment 54 includes a door flap secured with a bottom door latch 510. A strap 68 may be attached to the captive D-rings 512, 514 extending from lower compartment 54 to facilitate transportation of the portable defibrillator 10 and carrying case 500.

In the illustrative embodiment, injection molded rails 516, 518 are secured to frame 20 below side compartments 44, 32. Such rails enable the carrying case 500 to be sled mounted in EMT and other vehicles.

It should be understood that various changes and modifications of the embodiments shown in the drawings and described in the specification may be made within the spirit and scope of the present invention. Accordingly, it is intended that all matter contained in the above description and shown in the accompanying drawings be interpreted in an illustrative and not in a limiting sense. The invention is limited only as defined in the following claims and the equivalents thereto.

What is claimed is:

1. A carrying case for a defibrillator having a surface-mounted operational panel and an operational cable connected with the defibrillator, the carrying case comprising:
   a rigid sub-frame, the sub-frame comprising:
      first and second side walls and a back wall,
      a central floor cooperatively supported by the first and second side walls, the back wall attached to respective first ends of the first and second side walls, the central floor adapted to detachably mount the defibrillator; and
      a front wall and a third side wall, the third sidewall cooperatively connected with the back wall, the front wall and a second end of the second side wall to form a storage compartment; and
   a semi-rigid material wrapped around at least a portion of the sub-frame forming an outer shell of the carrying case, the outer shell enclosing the storage compartment and comprising a hinged access flap to access the storage compartment independently of accessing the surface-mounted operational panel.

2. The carrying case of claim 1, wherein the central floor is supported by the first and second side walls at a position which forms a second storage compartment between the central floor, the first and second side walls and the outer shell.

3. The carrying case of claim 2, wherein the outer shell comprises a second hinged access flap to access the second storage compartment.

4. The carrying case of claim 3, wherein the outer shell comprises a third hinged access flap to enclose said defibrillator.

5. The carrying case of claim 1, wherein the hinged access flap comprises a living hinge integrally formed with the outer shell.

6. The carrying case of claim 5, wherein the hinged access flap comprises a transparent portion for viewing contents of the storage compartment without opening the hinged access flap.

7. The carrying case of claim 1, wherein the second side wall has a cutout to pass the operational cable from the defibrillator into the storage compartment.

8. The carrying case of claim 1, wherein the storage compartment comprises a rigid floor.

9. The carrying case of claim 1, wherein:
   the second sidewall has a cutout to pass the operational cable from the defibrillator into the storage compartment;
   the hinged access flap comprises a transparent portion for viewing contents of the storage compartment without opening the hinged access flap; and
   the hinged access flap comprises a living hinge integrally formed with the outer shell.

10. A carrying case for a defibrillator having a surface-mounted operational panel and an operational cable connected with the defibrillator, the carrying case comprising:
    a rigid sub-frame, the sub-frame comprising:
       a central floor to detachably mount the defibrillator, and
       a storage compartment adjacently attached to the central floor, the storage compartment formed by a plurality of walls disposed transverse to the central floor; and
    a semi-rigid material wrapped around at least a portion of the sub-frame forming an outer shell of the carrying case, the outer shell enclosing the storage compartment and comprising a hinged access flap to access the storage compartment independently of accessing the surface-mounted operational panel.

11. The carrying case of claim 10, wherein one of said plurality of walls has a cutout to pass the operational cable from the defibrillator into the storage compartment.

12. The carrying case of claim 10, wherein the hinged access flap comprises a living hinge integrally formed with the outer shell.

* * * * *